(12) United States Patent
Christou et al.

(10) Patent No.: US 6,846,970 B1
(45) Date of Patent: Jan. 25, 2005

(54) TRANSFORMATION METHOD AND TRANSGENIC PLANTS PRODUCED THEREBY

(75) Inventors: Paul Christou, Norwich (GB); Ajay Kohli, Norwich (GB)

(73) Assignee: Plant Bioscience Limited, Norwich (GB)

( * ) Notice: Subject to any disclaimer, the term of this patent is extended or adjusted under 35 U.S.C. 154(b) by 0 days.

(21) Appl. No.: 09/611,736

(22) Filed: Jul. 7, 2000

Related U.S. Application Data

(60) Provisional application No. 60/144,513, filed on Jul. 19, 1999.

(51) Int. Cl.$^7$ .............................................. C12N 15/82
(52) U.S. Cl. ....................................... 800/293; 435/470
(58) Field of Search ................................ 800/293, 278, 800/298; 435/470, 320.1, 419, 468

(56) References Cited

FOREIGN PATENT DOCUMENTS

EP        1 174 513 A      1/2002

OTHER PUBLICATIONS

Schnorf et al, "An improved approach for transformation of plant cells by microinjection: molecular and genetic analysis", 1991, Transgenic Research, vol. 1, pp. 23–30.*

Dehio et al, "Identification of plant genetic loci involved in a posttranscriptional mechanism for meiotically reversible transgene silencing", Jun. 1994, Proc. Natil. Acad. Sci., vol. 91, pp. 5538–5542.*

Richard D. Palmiter, et al., "Germ–Line Transformation of Mice", Annual Reviews, Inc., 1986, pp. 465–499.

Porsch Petra et al., "A plant transformation vector with a minimal T–DNA II. Irregular integration patterns of the T–DNA in the plant genome", Plant Molecular Biology, vol. 37, No. 3, pp. 581–585, Jun. 1998, XP–002174098.

Christou P. et al., "Production of transgenic rice (Oryza sativa L.) plants from agronomically important indica and japonica varieties via electric discharge particle acceleration of exogenous DNA into immature zygotic embryos", Bio/Technology, vol. 9, No. 10, pp. 957–962, 1991, XP009025024.

Cooley, J. et al., "Molecular and genetic characterization of elite transgenic rice plants produced by electric–discharge particle acceleration", Theoretical and Applied Genetics, vol. 90, No. 1, pp. 97–104, 1995, XP009025005.

Kohli, Ajay et al., "Transgene organization in rice engineered through direct DNA transfer supports a two–phase integration mechanism mediated by the establishment of integration hot spots" Proceedings of the National Academy of Sciences of the United States, vol. 95, No. 12, pp. 7203–7208, Jun. 9, 1998, XP–002268628.

Kononov, M. et al., "Integration of T–DNA binary vector [backbone] sequences into the tobacco genome: evidence for multiple complex patterns of integration", Plant Journal, vol. 11, No. 5, pp. 945–957, May 7, 1997, XP–002052140.

Fu, Xiangdong et al., "Linear transgene constructs lacking vector backbone sequences generate low–copy–number trangenic plants with simple integration patterns", Transgenic Research, vol. 9, No. 1, pp. 11–19, Feb. 2000, XP–001087792.

* cited by examiner

*Primary Examiner*—Elizabeth F. McElwain
*Assistant Examiner*—Cynthia Collins
(74) *Attorney, Agent, or Firm*—Fulbright & Jaworski LLP

(57) ABSTRACT

This invention relates to methods for producing, at a high frequency, transgenic plants that contain little if any vector sequences, have simple integration patterns, contain few copies of the transgene at each locus, express the transgene at all stages of development and do not exhibit transgene silencing. The method comprises introducing minimal transgene expression cassettes, which are substantially or totally devoid of vector sequences, by direct DNA transfer, preferably by particle or microprojectile bombardment. This invention also relates to transformed plant cells, the transgenic plants regenerated therefrom, and subparts of the transgenic plants produced by the methods of this invention. The invention also includes all progeny and subsequent progeny (i.e., all subsequent generations) derived from primary transformants through selfing or crossing.

43 Claims, 3 Drawing Sheets

SEQUENCE LISTING

<160> NUMBER OF SEQ ID NOS: 10

<210> SEQ ID NO 1
<211> LENGTH: 4
<212> TYPE: PRT
<213> ORGANISM: artificial sequence
<220> FEATURE:
<223> OTHER INFORMATION: ER retention signal sequence

```
<400> SEQUENCE: 1

Lys Asp Glu Leu
1

<210> SEQ ID NO 2
<211> LENGTH: 4
<212> TYPE: PRT
<213> ORGANISM: Artificial Sequence
<220> FEATURE:
<223> OTHER INFORMATION: ER retention signal sequence

<400> SEQUENCE: 2

His Asp Glu Leu
1

<210> SEQ ID NO 3
<211> LENGTH: 12
<212> TYPE: DNA
<213> ORGANISM: artificial sequence
<220> FEATURE:
<223> OTHER INFORMATION: Oligonucleotide encoding KDEL

<400> SEQUENCE: 3
aaagatgagc tc                                                          12

<210> SEQ ID NO 4
<211> LENGTH: 12
<212> TYPE: DNA
<213> ORGANISM: artificial sequence
<220> FEATURE:
<223> OTHER INFORMATION: Oligonucleotide encoding HDEL

<400> SEQUENCE: 4
catgatgagc tc                                                          12

<210> SEQ ID NO 5
<211> LENGTH: 5
<212> TYPE: PRT
<213> ORGANISM: artificial sequence
<220> FEATURE:
<223> OTHER INFORMATION: Linker sequence

<400> SEQUENCE: 5

Gly Gly Gly Gly Ser
1               5

<210> SEQ ID NO 6
<211> LENGTH: 4
<212> TYPE: PRT
<213> ORGANISM: artificial sequence
<220> FEATURE:
<223> OTHER INFORMATION: Linker sequence

<400> SEQUENCE: 6

Arg Gly Ser Glu
1

<210> SEQ ID NO 7
<211> LENGTH: 13
<212> TYPE: DNA
<213> ORGANISM: artificial sequence
<220> FEATURE:
<223> OTHER INFORMATION: SfiI recognition site
<221> NAME/KEY: misc_feature
<222> LOCATION: (5)..(9)
<223> OTHER INFORMATION: N is any nucleotide
```

-continued

```
<400> SEQUENCE: 7
ggccnnnnnc cgg                                                        13

<210> SEQ ID NO 8
<211> LENGTH: 20
<212> TYPE: DNA
<213> ORGANISM: artificial sequence
<220> FEATURE:
<223> OTHER INFORMATION: Primer that binds CaMV promoter

<400> SEQUENCE: 8
tacagtctca gaagaccaaa                                                 20

<210> SEQ ID NO 9
<211> LENGTH: 20
<212> TYPE: DNA
<213> ORGANISM: artificial sequence
<220> FEATURE:
<223> OTHER INFORMATION: Primer that binds to Nos terminator

<400> SEQUENCE: 9
aatcatcgca agaccggcaa                                                 20

<210> SEQ ID NO 10
<211> LENGTH: 21
<212> TYPE: DNA
<213> ORGANISM: artificial sequence
<220> FEATURE:
<223> OTHER INFORMATION: Primer that binds to 3' end of gusA coding
      sequence

<400> SEQUENCE: 10
gggaggctac agatgctttg c                                               21
```

TRANSFORMATION METHOD AND TRANSGENIC PLANTS PRODUCED THEREBY

This application claims priority from U.S. Ser. No. 60/144,513, filed Jul. 19, 1999 and incorporated herein in its entirety.

FIELD OF THE INVENTION

This invention relates to methods for producing transgenic plants at a high efficiency wherein the transgenic plants contain little if any vector sequences, exhibit simple transgene integration patterns, have the transgene integrated at only one or a few integration sites, contain few copies of the transgene at each integration site, and stably express the transgene at all stages of development. Few if any of the transgenic plants produced by this method exhibit transgene silencing. The method comprises introducing "minimal transgene expression cassettes", which are expression cassettes substantially devoid of vector sequences, by direct DNA transfer techniques, particularly particle bombardment, of intact plant cells.

BACKGROUND OF THE INVENTION

It is now a routine procedure to generate transgenic plants, either through Agrobacterium-mediated transformation or direct DNA transfer methods (Gelvin, *Curr. Opin. Biotechnol.*, 9:227–232 (1998); Komari et at., *Curr. Opin. Plant Biol.*, 1:161–165 (1998); Tyagi et al., *Crit. Rev. Biotechnol.*, 19:41–79 (1999)). Many commercially important dicot and monocot species have been transformed. However, while the transformation procedure itself is no longer considered a limiting step, the recovery of useful transgenic lines is hampered by variable transgene expression levels and transgene silencing (Flavell, *Proc. Natl. Acad. Sci. USA*, 91:3490–3496 (1994); Finnegan, *Ann. Rev. Plant Physiology*, 49:223–247 (1998)). Complete or partial transgene silencing has been attributed to a number of factors including the copy number of the integrated genes (Matzke and Matzke, Plant Physiol., 107:679–685 (1995) and Matzke et al. *Mol. Gen. Genet.*, 244:219–229 (1994)), the position of transgene integration (Hobbs et al., *Plant Mol. Biol.*, 15:851–864 (1990); Peach and Velten, *Plant Mol. Biol.*, 17:49–60 (1991); Matzke and Matzke, *Curr. Opin. Plant Biol.*, 1:142–148 (1998)), the configuration and structure of the transgenic locus (Stam et al., *Plant J.*, 12:63–82 (1997)), the structural integrity of individual transgenes (Kohli et al., 1998) and the genetic properties of the host plant, (e.g., genetic background, ploidy and zygosity) (Beaujean et al., *Mol. Gen. Genet.*, 260:362–371 (1998)).

Whole plasmid transformation is still almost universal in plant systems. This may trace its roots to the requirement for Agrobacterium vector sequences in Agrobacterium-mediated transformation. The Agrobacterium vector carries essential vir genes required for T-DNA excision, transfer and integration. In previously described transformation methods, the transgene cassette encoding a desired product is cloned into a vector, e.g., a plasmid, a virus or an Agrobacterium Ti plasmid, and the entire vector containing the transgene cassette is introduced into the plant cell. However, vector sequences serve no required purpose for DNA transfer and integration in direct DNA transfer procedures such as, e.g., particle bombardment. The methods of this invention generate transgenic plants that display stable transgene expression at a higher frequency than produced by previously described methods. In embodiments wherein two or more transgenes are simultaneously introduced into the plants, the frequency of transgene co-expression is higher than the frequency of co-expression produced by previously described methods. The transgenic plants produced by the methods described herein exhibit simple integration patterns, low copy number of the transgene and in general do not exhibit transgene silencing.

DETAILED DESCRIPTION OF THE INVENTION

Figure 1:
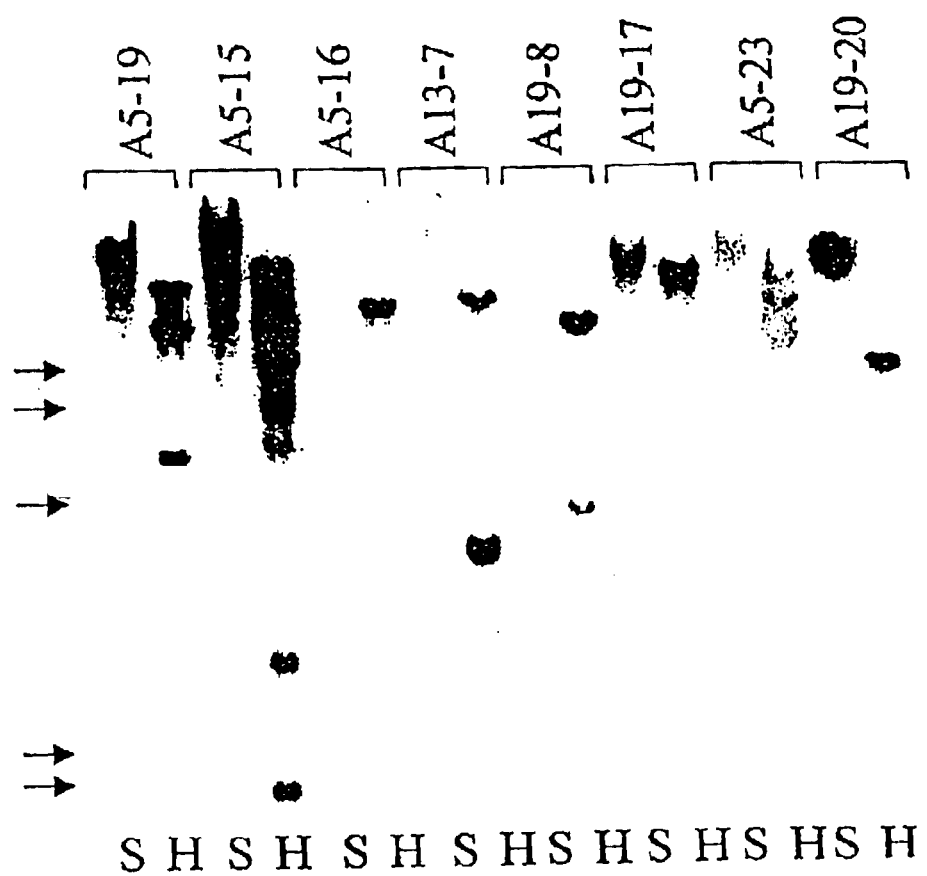
FIG. 1 depicts a Southern blot of genomic DNA from bar-transgenic rice plants, digested with the 'non-cutter' SfiI (S) or with HindIII (H), which cuts once within the transgene cassette and hybridized with a bar probe.

An undesirable property of vector backbone sequences is their tendency to promote transgene rearrangements. The involvement of the vector backbone in vector-vector recombination events has been reported by several groups, and a number of recombination hotspots have been identified that stimulate illegitimate recombination through the formation of stable secondary structures. One particular hotspot is the vector's origin of replication, which may represent a target for the nucleases and topoisomerases involved in illegitimate recombination events. Indeed, consensus topoisomerase sites are often found near vector-vector and vector-genomic recombination junctions in plants and animals. Another disadvantage of transforming plants with nucleic acid molecules comprising vector sequences is the concern that new replicons, comprising vector origins of replication and plant genomic DNA, may escape into the environment. Furthermore, recombinogenic elements in the vector backbone may be responsible for complex vector multimerization events also involving segments of genomic DNA, resulting in the integration of large transgene complexes. Multiple transgene copies are undesirable, as high copy number is thought to inhibit transgene expression and contribute to transgene silencing. Additionally, very large transgenic loci can be meiotically unstable, leading to excision of the locus and loss of transgene expression in subsequent generations. Thus, vector backbone sequences are undesirable as well as superfluous in direct DNA transfer procedures.

Therefore, it is desirable to generate transgenic plants with low transgene copy numbers, small transgenic loci, little or no transgene silencing and stable transgene expression. The methods described herein achieve these results by transforming plant cells with minimal transgene expression cassettes, which are DNA expression cassettes substantially devoid of vector sequences, and direct DNA transfer techniques. This is the first report of stable transgenic plants containing an expression cassette devoid of sequences from the vector into which it was originally cloned.

The frequency of transgenic plant lines with simple, low copy integration events is much greater for the plants generated by the methods of this invention, i.e., plants regenerated from cells that were transformed with minimal transgene expression cassettes and direct DNA transfer techniques, as compared to plant cells that were transformed with supercoiled or linearized vectors, e.g., plasmids. This is true for both selected and non-selected transgenes. While the co-transformation efficiency is essentially the same between the minimal transgene expression cassettes and plasmid constructs, the incidence of transgene silencing is much lower and the co-expression frequency for multiple transgenes is significantly higher for those plants produced by the methods of this invention as compared to previously described methods. We discuss these results infra in relation to co-transformation experiments with minimal transgene expression cassettes comprising selectable marker genes and cassettes encoding products of agronomic interest.

One embodiment of this invention is a heterogenous population of transgenic plants wherein at least 70% of the transgenic plants have a simple transgene integration pattern and a low rate of transgene silencing. Preferably, the rate of transgene silencing is less than 20% of the transgenic plants having a simple integration pattern, more preferably less than 5% undergo transgene silencing and most preferably none of the population of transgenic plants having simple integration patterns undergo transgene silencing.

Also an embodiment of this invention is a method for transforming plant cells by direct DNA transfer, particularly particle bombardment, with one or more minimal transgene expression cassettes. Minimal transgene expression cassettes are expression cassettes consisting essentially of a transgene comprising a nucleic acid sequence that encodes a desired product such as, e.g., an enzyme, a mammalian or avian protein, e.g., an antibody or a growth factor, or a factor for resistance to an antibiotic or herbicide, or an antisense RNA, in operable linkage with sequences that regulate the expression of the nucleic acid sequence. The minimal transgene expression cassette comprises at least one transgene comprising at least a promoter in operable linkage with a nucleic acid molecule having a sequence that encodes a desired product and may also comprise an operator, an enhancer, a terminator, or a polyadenylation signal, etc. that regulate the expression of the transgene(s). The minimal transgene expression cassette is substantially devoid of sequences that do not encode or regulate the expression of the desired product. For example, less than about 10–15% of the minimal transgene expression cassette sequences are vector sequences, i.e., nucleotide sequences that do not encode a desired product or regulate the expression of that product. Preferably, less than about 50 base pairs of the minimal transgene expression cassette are vector sequences. More preferably, the minimal transgene expression cassette comprises less than about 20 base pairs that are vector sequences. Most preferably, the minimal transgene expression cassette is completely devoid of nucleotide sequences that are not part of an element that encodes the transgene(s) product(s) or regulates expression of the transgene(s) product(s) of interest.

The methods of this invention efficiently produce transgenic plants that contain little if any vector sequences, exhibit simple integration patterns, have the transgene integrated at only one or a few integration sites, contain few copies of the transgene at each integration site, and stably express the transgene at all stages of development.

A simple integration pattern reflects at least one and no more than about five integration sites within the genome of the transgenic plant, wherein each integration site has at least one and no more than about five copies of the transgene inserted at each site. Preferably, there are no more than three integration sites in the plant genome. More preferably, there is no more than one integration site in the plant genome. Preferably, there are at least one and no more than three copies of each transgene in each integration site. More preferably, there is one copy of each of the transgenes that are present at an integration site.

The simple transgene integration pattern may be detected on a Southern blot. For example, a Southern blot prepared from samples of transgenic plant genomic DNA digested with (1) a restriction enzyme that does not have a recognition site within the transgene cassette prior to its integration into the plant DNA and that only infrequently cuts the plant genomic DNA and (2) a restriction enzyme that has a single restriction site within the transgene cassette. An enzyme that only infrequently cuts genomic DNA produces genomic DNA fragments of at least about 64 kb. An example of such an "infrequent cutter" is a restriction enzyme which recognizes an eight base pair sequence. The Southern blot of the digested DNA hybridized to a transgene specific probe under stringent conditions (e.g., 2×SSC, 0.5% SDS at 65° C. for 20 minutes and 0.2×SSC, 0.5% SDS at 65° C. for 20 minutes, or equivalent stringency conditions) displays a simple integration pattern. The simple integration pattern is manifested as only one to about three bands of hybridizing DNA for the genomic DNA digested with the enzyme that does not have a recognition site in the transgene and these bands resolve into only one to about three bands for the genomic DNA digested with the enzyme that has a single recognition site within the transgene cassette.

The methods of this invention efficiently produce transgenic plants wherein the transgene is stably expressed in the plant tissue. Preferably, at least about 70% of transgenic plants generated from the transformed plant cells stably express the transgene and this stable expression is inherited by the progeny of the transgenic plants. Also contemplated within the scope of this invention are progeny plants having stable expression of the transgenes and their production by classical crossing of two transgenic plants produced by the methods of this invention.

Plants, which include a plant cell according to the invention, are also provided, along with any part or propagule thereof, seed, selfed or hybrid progeny and descendants. A plant according to the present invention may be one which does not breed true in one or more properties. Plant varieties may be excluded, particularly registrable plant varieties according to Plant Breeders' Rights. It is noted that a plant need not be considered a "plant variety" simply because it contains stably within its genome a transgene, introduced into a cell of the plant or an ancestor thereof.

Plant cells may be transformed with the minimal transgene expression cassette by using any suitable direct DNA transfer technology, such as, e.g., particle or microprojectile bombardment (U.S. Pat. No. 5,100,792, EP-A444882, EP-A-434616, incorporated herein by reference), microinjection (WO 92/09696, WO 94/00583, EP 331083, EP 175966, Green et al., *Plant Tissue and Cell Culture*, Academic Press (1987) all incorporated herein by reference), electroporation (EP 290395, WO 87/06614 incorporated herein by reference), liposome mediated DNA uptake (e.g., Freeman et al., *Plant Cell Physiol.*, 29:1353 (1984) incorporated herein by reference), the vortexing method (Kindle, *PNAS USA*, 87:1228(1990), incorporated herein by reference), silicon carbide fibers (U.S. Pat. No. 5,302,523 incorporated herein by reference) and other forms of direct DNA uptake (DE 4005152, WO 9012096, U.S. Pat. No. 4,684,611, all incorporated herein by reference). For a review of physical methods for the transformation of plant cells see, e.g., Oard, *Biotech. Adv.*, 9:1–11 (1991). Preferably, the plant cells are transformed by particle or microprojectile bombardment.

Those of skill in the art appreciate that different methods may be used for the regeneration of transgenic plants from transformed cells in culture. A plant may be regenerated, e.g., from single cells, callus tissue (Type I or Type II), leaf discs, and immature or mature embryos, hypocotyls and cotyledons, as is standard in the art. Almost any plant, e.g., rice, wheat, corn, oat, barley, sorghum, legumes, and woody species, can be entirely regenerated from cells, tissues and organs of the plant. The generation of fertile transgenic plants has been achieved in cereals, e.g., rice, maize, wheat, oat, and barley (reviewed in Shimamoto, K., *Current Opinion in Biotechnology*, 5:158–162 (1994); Vasil et al. *Bio/Technology*, 10:667–674, (1992); Vain et al., *Biotechnology Advances*,13:4:653–671, (1995); Vasil, *Nature Biotechnology*, 14, page 702 (1996)). Available techniques are also reviewed in Vasil et al., *Cell Culture and Somatic Cell Genetics of Plants*, Vol I, II, and III, Laboratory Procedures and Their Applications, Academic Press, (1984), Weissbach and Weissbach, *Methods for Plant Molecular Biology*, Academic Press, (1989) and also Christou, *Plant Mol. Biol.* 163:39–44 (1997); Cao et al., *Plant Gene Transfer, UCLA Symposium Molecular and Cellular Biology*, 129:21–33 (1990), D'Halluin et al., *Plant Cell*, 4:1495–1505 (1992), and Lowe et al., *Bio/Technology* 13:677–682 (1995) (all incorporated herein by reference).

The minimal transgene expression cassette may contain one or more genetic marker genes, "genetic markers." Those of skill in the art will appreciate that there are many different kinds of genetic markers that may be incorporated into the minimal transgene expression cassette and that the usefulness of a genetic marker is dependent on the host system where the marker is to be expressed. Selectable genetic markers useful in this invention include any gene that encodes a product which provides for a growth advantage of transformed plant cells or a growth advantage of transgenic plants that are regenerated from those cells. For example, the product may confer resistance to an antibiotic, a herbicide, or a metabolic inhibitor. Selectable genetic markers may be chimeric genes that confer selectable phenotypes such as, e.g., resistance to antibiotics such as kanamycin, hygromycin, phosphinothricin, chlorosulfuron, methotrexate, gentamycin, spectinomycin, streptomycin, methotrexate, imidazolinones, and glyphosate. The selectable marker may encode, e.g., phosphinothricin acetyltransferase (pat) (De Block et al., *EMBO J*. 6:2513–2518 (1987)), hygromycin phosphotransferase (hpt) (Datta et al., *Bio/Technology* 8:736–740 (1990)) and other enzymes such as, e.g., neomycin phosphotransferase, kanamycin phosphotransferase, epsp synthase, acetolactate synthase and mannose isomerase. Preferably, the selectable genetic marker is the bar or hpt gene. The genetic marker may also be a nucleic acid molecule that encodes a product that does not confer a growth advantage under particular conditions but allows one to identify, "screen for", the plants that have incorporated the genetic marker, e.g., it does not provide for resistance to a cytotoxic or cytostatic compound but encodes a "screenable" product, such as, e.g., luciferase (luc), green fluorescent protein (Gfp) or beta-glucuronidase (gusA).

The minimal transgene expression cassette may comprise one or more nucleic acid sequences which encode a product of interest, e.g., a predesigned synthetic polypeptide (see for example U.S. Pat. No. 5,811,654), an enzyme, a growth factor, a cell surface receptor molecule, a seed storage protein, a fungicide, or fragments thereof, an antibody or fragment thereof e.g., Fab', F(ab')$_2$, single chain Fv fragments, bispecific single chain Fv fragments and diabodies, in operable linkage with a promoter and may further comprise an operator, an enhancer, a termination sequence, a polyadenylation sequence or other flanking sequences that regulate the expression of that product within plants. The transgene may comprise any promoter suitable for expression in plant cells and may have plant or non-plant origins, e.g., mammalian, bacterial or viral promoters. Suitable promoters include, for example, a seed specific promoter, a chloroplast specific promoter, a cytosol specific promoter, a leaf, stem or root-specific promoter, a lectin gene promoter, an opine synthase gene or a ribulose-1,5-bis-phosphate carboxylase small subunit gene promoter, an osmotin gene promoter, a promoter for Peanut Chlorotic Streak Caulimovirus (PCLSV), an endosperm specific promoter, isocitrate lyase promoter, the pea ENOD12 nodulin promoter and a barley alpha amylase promoter. The promoter may be a constitutive promoter, such that expression occurs throughout plant tissue(s) or throughout development, or both, or an inducible or tissue specific promoter that is differentially expressed within the plant tissue(s) either spatially or temporally during development. Preferably the promoter is a CaMV 35s promoter (Gardner et al., *NAR*, 9:2871–2888 (1981)), a ubiquitin promoter, low molecular weight glutenin promoter (Colot et al., *EMBO J.*, 6:3559–3564 (1987)) or a glutetin-1 promoter. (See, e.g., U.S. Pat. Nos. 5,352,605; 5,359,142; 5,424,200; 5,510,474; 5,614,399; EP342 926 B1; U.S. Pat. No. 6,020,190; WO 98/10062; U.S. Pat. Nos. 5,689,040; 5,693,506; 5,391,725; 5,646,333; 5,034,322; 5,850,018; 5,837,849; 5,874,626; 5,850,019; 5,866,763; 5,866,792; 5,589,325; 5,589,331; 5,859,336, and; 5,830,724 which all disclose promoters which function in plants).

The transgene may also comprise any terminator and polyadenylation signal that to is suitable for plant cells. Preferably the terminator is a Nopaline synthase (nos) terminator, a Rubisco small subunit(ssu) terminator and a CaMV terminator.

The minimal transgene expression cassette may encode a chimeric product comprising, e.g., a leader peptide or a retention signal or both. Suitable leader peptides include, e.g., prokaryotic or eukaryotic leader peptides such as, e.g., an amylase leader or a mammalian antibody leader peptide. Suitable retention signals include, e.g., an endoplasmic reticulum (ER) retention signal such as, e.g., a peptide with the amino acid sequence, Lys Asp Glu Leu (KDEL) (SEQ ID NO: 1) or His Asp Glu Leu (HDEL) (SEQ ID NO: 2). KDEL may be encoded by the nucleotide sequence 5'-AAA GAT GAG CTC-3'(SEQ ID NO: 3) and HDEL may be encoded by 5' CAT GAT GAG CTC 3'(SEQ ID NO: 4). Other sequences encoding the KDEL or HDEL but differing from these nucleotide sequences by virtue of degeneracy of the genetic code may be employed. The KDEL or HDEL encoding sequence may be operably linked to a coding sequence for a polypeptide to provide for a fusion of the polypeptide and the ER retention signal. Generally the retention signal is placed at the C-terminus of the polypeptide although it can be placed at other positions with the polypeptide sequence. The ER-retention signal may be preceded by a linker sequence, such as, e.g., (Gly)$_4$Ser (SEQ ID NO: 5) and/or Arg Gly Ser Glu (RGSE) (SEQ ID NO: 6) (Wandelt et al., *Plant J*. 2(2): 181–192 (1992)).

A leader peptide may be used to direct the product to a particular cellular compartment. The leader peptide may be of mammalian origin, and may be murine, such as an immunoglobulin light or heavy chain leader peptide. The nucleotide sequence used in the construct to encode the leader peptide may be codon optimized for expression in the plant of interest, preferably monocot, e.g., rice, wheat, corn or barley. A preferred leader peptide useful in accordance with this aspect of the present invention is that of the TMV virion specific mAb24 (Voss et al. *Mol Breed*, 1:39–50 (1995)). Modified forms may also be employed. As with other elements for use in expression cassettes in accordance with various aspects of the present invention, the coding sequence may be codon optimized for monocot codon usage according to Angenon et al. (*FEBS*, 271:144–146 (1990)). The leader peptide may be vacuole targeting signal, such as the leader peptide of a strictosidine synthase gene, e.g., that of the *Catharanthus roseus* strictosidine synthase (McKnight et al. (1990) or of *Rauwolfia serpentina* strictisodine synthase (Kutchan et al. *FEBS Lett*, 237 40–44 (1988)). For a review of vacuole targeting sequences, see Neuhaus *Plant Physiol. Biochem.*, 34(2):217–221 (1996). The leader peptide may be a chloroplast targeting signal such as of the pea rubisco leader peptide sequence (Guerineau et al. *NAR*, 16:11:380 (1988)). For a review of chloroplast targeting peptides see van Heijne et al. (*Eur. J. Biochem.* 180:535–545 (1989)) or Kavanagh et al. (*MGG*, 215:38–45 (1988)) or Karlin-Neumann et al. (*EMBO J.*, 5:9–13 (1986)). The leader peptide may be a 5' sequence of a seed storage protein, dicot or monocot, causing transport into protein bodies, such as the *Vicia fabia* legumin B4 leader (Baeumlein et al., *Mol. Gen. Genet.*, 225:121–128 (1991)).

In one embodiment of the invention, the minimal transgene expression cassette comprises more than one transgene encoding a desired product. Those of skill in the art will appreciate that as the size of the minimal transgene expression cassette increases, the size of the transgenic loci are also likely to increase. However, there is no evidence to link the phenomenon of gene silencing to the size of the initial transforming DNA.

The minimal transgene expression cassette may be isolated from any suitable vector, e.g., plasmid, phagemid or viral vector, that is known in the art. Those of skill in the art are well acquainted with various protocols for the isolation and purification of nucleic acid molecules (See, e.g., Rogers and Bendich, in *Plant Molecular Biology Manual*, 2$^{nd}$ Ed. 1:1–8 (1994), incorporated herein in its entirety by reference). For example, a vector may be digested with one or more restriction enzymes and the digested DNA electrophoresed through an SDS polyacrylamide gel or agarose gel and the appropriate DNA fragment isolated from the gel using the Quiaquick™ gel extraction kit (Quiagen Ltd. Boundary Court, Gatwick Road Crawley, West Sussex RH10 2AX (UK)) according to the manufacturer's instructions or purified by other methods such as liquid chromatography (LC) or high pressure liquid chromatography (HPLC), etc.

Another aspect of this invention is a population of transformed plant cells produced by the method of this invention and the population of transgenic plants regenerated from those population of transformed cells. Those of skill in the art will appreciate that the population of transgenic plants regenerated from the population of transformed plant cells will be comprised of non-identical plants because the transgene does not necessarily integrate into the same site in each plant cell during transformation. Thus, another aspect of this invention is a population of non-identical transgenic plants produced by the methods of this invention wherein at least about 60% of the population of transgenic plants have simple integration patterns of the integrated transgene cassette and stably express the transgene. Preferably, at least about 70% of the population of transgenic plants have a simple transgene cassette integration pattern and stably express the transgene. At least about 40% of the transgenic plants have the transgene cassette integrated in at most three integration sites.

Figure 2:
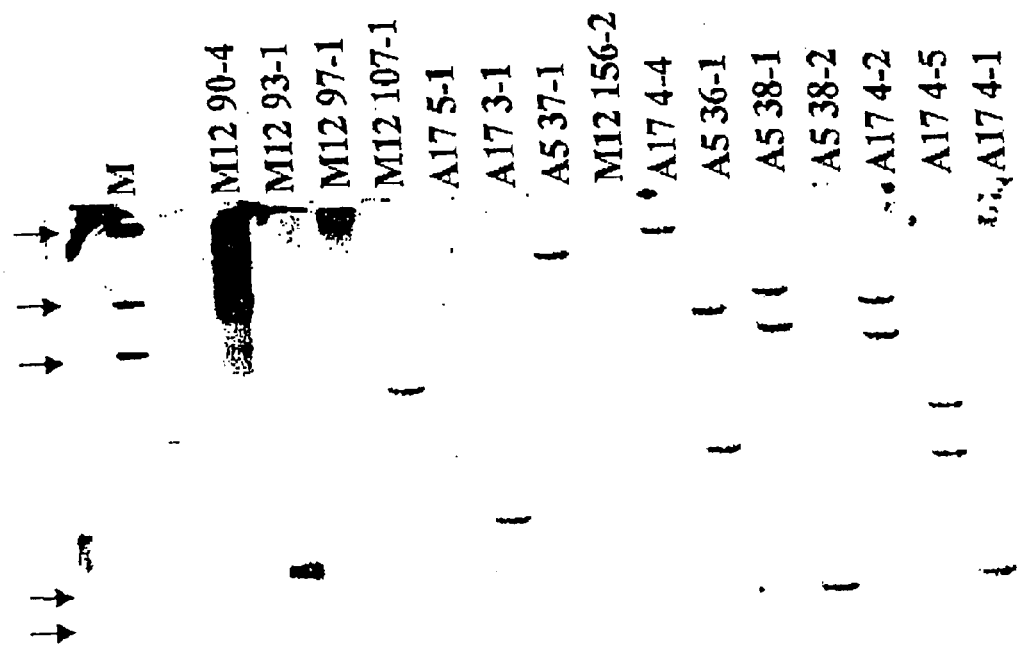
FIG. 2 depicts a Southern blot of genomic DNA from hpt-transgenic rice plants, digested with SalI, which cuts at the 3'-end of the transgene cassette, and hybridized with an hpt probe. M=markers.
Figure 3:
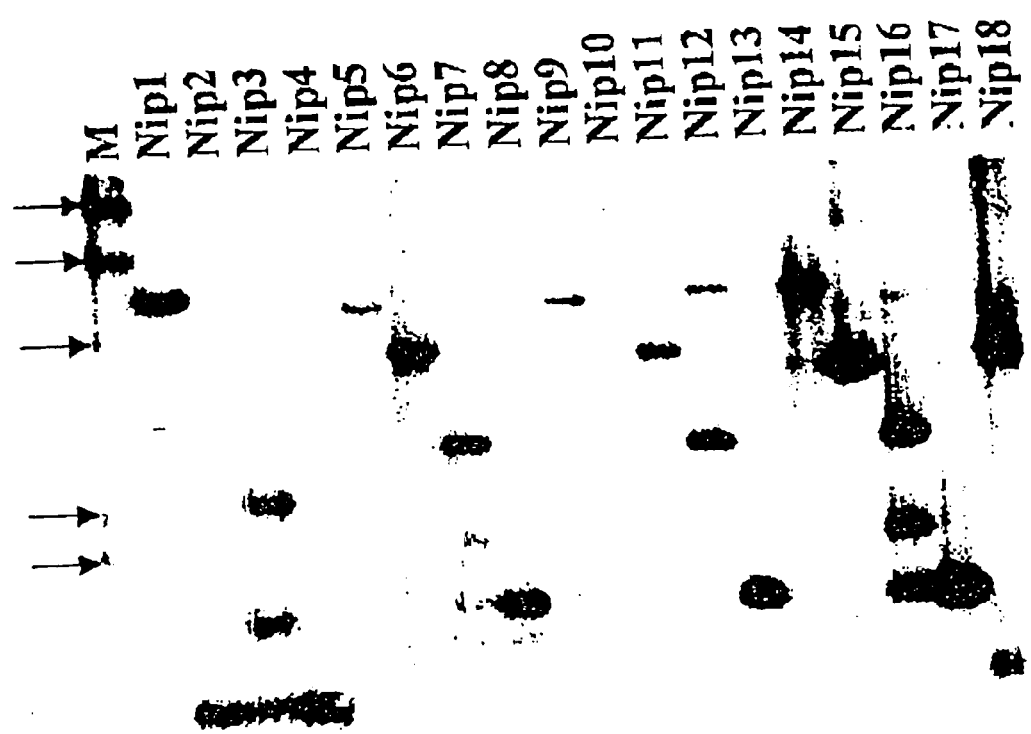
FIG. 3 depicts a Southern blot of genomic DNA from 18 hpt-gusA-transgenic rice plants, digested with NcoI, which cuts at the 5'-end of the transgene cassette, and probed with a gusA probe. M=markers.

The transgenic plant lines obtained from transformed plant cells produced by bombardment with minimal transgene cassettes display a reduced frequency of rearrangement events (see, e.g., FIGS. 1, 2, and 3). In most of the plants, 1–3 bands detected on Southern blots of genomic DNA digested with restriction enzymes having a six base recognition site (6 base cutters) indicate the presence of 1 to about 5 transgene copies. Lines with more copies were rare. Without wishing to be bound by theory the integration of multiple copies of minimal transgene expression cassettes that do not contain extensive regions of vector sequences could occur in several ways. Firstly, different cassettes could integrate simultaneously at a damaged chromosomal region that has attracted several DNA repair complexes. In such a case, the cassettes might be interspersed with genomic DNA. Secondly, the cassettes might undergo illegitimate end-joining prior to integration, and integrate as a unit, in which case the cassettes would be contiguous. Finally, as discussed recently by Kohli et al. (*Proc. Natl. Acad. Sci. USA*, 95:7203–7208 (1998)), a single integrated transgene may undergo recombination with exogenous DNA either because the exogenous DNA is attracted to repair complexes forming at the integration site, or because recombination occurs between homologous sequences in the integrated transgene and exogenous DNA. In methods that use nucleic acid molecules with extensive vector sequences, such homologous sequences are usually vector backbone sequences, but in this case a sequence within the transgene cassette must be responsible. Kohli et al. (*Plant J.*, 17:591–601 (1999)) demonstrated that a potential cruciform structure surrounding the TATA-box of the CaMV 35S promoter (which is used in some of the constructs in the Examples) generated a recombination hotspot that was involved in more than 40% of the recombination junctions characterized.

SfiI recognizes the 8 bp sequences 5'-GGCCNNNNNCCGG-3'(SEQ ID NO: 7), and does cut the transgene expression cassettes of Example I prior to their integration into the plant genome. Southern blots of genomic DNA isolated from plants transformed with any of the transgenic cassettes disclosed in Example 1 and digested with the non-cutter SfiI typically displayed a single band, suggesting that the integration site, the region of the plant genome where the copies of the transgene integrated, was on average smaller than 65 kbp (FIG. 1). However, the presence of multiple bands after the digestion of genomic DNA with other non-cutters (restriction endonucleases that do not have recognition sites within the transgene prior to integration in the plant genome) suggest one or two possibilities: a) de novo creation of restriction enzyme recognition sites as a result of rearrangement; or b) capture of genomic DNA between transgenic sequences before or during integration (see, e.g., Salomon and Puchta, "Capture of genomic and T-DNA sequences during double-strand break repair in somatic plant cells", *EMBO*, 17(20):6086–6095 (1998)). The interspersal of genomic DNA between transgene sequences was reported earlier by Kohli et al. (1998; supra) and Pawlowski and Somers, "Transgenic DNA integrated into the oat genome is frequently interspersed by host DNA", *PNAS*, 95(21):12106–12110 (1998).

In addition, Southern blots demonstrated that about 80% of the transgenic plant to lines in Example 1 generated from cells bombarded with a single transgenic cassette, e.g., the hpt cassette displayed very simple integration patterns (only one or two bands on Southern blots of genomic DNA digested with an infrequent cutter). Southern blots, hybridized with a gusA specific probe, of genomic DNA from transgenic plants, which were generated from cells co-bombarded with the gusA and hpt cassettes and selected for hygromycin resistance also displayed simple integration patterns. This demonstrates that the recovery of a high proportion of plants with simple integration patterns was not due to selection pressure since there was no selection for gusA. In contrast, Southern blots of genomic DNA from plant lines generated by particle bombardment with supercoiled plasmids demonstrated that only 20 to 30% of the plant lines had simple integration patterns. The results presented herein demonstrate that the use of linear, minimal transgene expression cassettes rather than supercoiled or relaxed plasmids leads to the generation of transgenic plants with simple integration patterns, low transgene copy numbers and few cases of transgene rearrangement.

The methods described herein for the delivery and integration of minimal transgene expression cassettes also ensures high expression levels and reduction of the silencing phenomenon. Expression analysis of the transgenic plants of this invention at different growth stages failed to detect transgene silencing, which is a common phenomenon for high copy number transgenes.

Transgene expression in essentially all transgenic plants generated by the process of this invention is stable and heritable. This is in contrast to previous reports which disclose that typically about 20–30% of the transgenic plants produced by particle bombardment with whole plasmid DNA have low levels of transgene expression or full transgene silencing, even though some of these transgenic plants have simple integration patterns (Elmayan T. and Vaucheret H., "Expression of single copies of a strongly expressed 35S transgene can be silenced post-transcriptionally, *Plant Journal*, 9(6): 787–797 (1996)).

Although there is a reduced frequency of complex rearrangement patterns of the transgenes in the transgenic plants of this invention (FIG. 1), the transgene cassette itself may still undergo recombination and rearrangement. Certain of the transformed plant lines generated by the method of this invention contain multiple copies of the transgene cassette at the single locus. However, in most transgenic plants produced by this method, the copy number of the transgene does not exceed three in total per genome. Transgenic plant lines with a copy number of more than three were very few.

Example 1 displays the results of transforming plant cells with a bar gene minimal transgene expression cassette. Twenty-six independent transgenic plants were regenerated from the bar-transformed cells and only three of the twenty-six displayed complex integration patterns of the bar gene. All copies of the bar gene were located at single locus in these three lines and high levels of phosphinothricin acetyltransferase (PAT) expression were also detected in these three lines.

The expression of PAT was analyzed in all 26 lines at different developmental stages (seedling, vegetative, and reproduction) of the $T_0$ plants to see if transgene silencing occurred at any stage. No transgene silencing was detected in the low copy number lines or in the high copy number lines. These results conclusively prove the advantages of generating transgenic plants using the minimal sequences required for expression of a transgene.

Some of the transgenic plant lines, whether transformed with an hpt minimal transgene cassette or a bar minimal transgene cassette, have a complex integration pattern and in some cases the plant lines have multiple copies of the minimal transgene expression cassette integrated at the same locus. These results suggest that the mechanisms involved in integration of minimal transgene expression cassettes and linearized or supercoiled vectors may be similar, in at least some cases.

Direct DNA transfer techniques, particularly particle bombardment, provides for the simultaneous delivery of multiple nucleic acid molecules encoding different products, e.g., products of agronomic relevance, to economically-important crop plants. When used in the method of this invention the simultaneous delivery of two minimal transgene cassettes, i.e., hpt and gusA minimal transgene expression cassettes, by particle bombardment resulted in 100% co-transformation.

In Example 1, particle bombardment-mediated transformation was used to deliver minimal transgene expression cassettes comprising a transgene, either bar or hpt, into rice embryos. Transgenic plants were then regenerated from the bar and hpt transformed rice embryos. Nearly 100% of the transgenic plants produced by this method expressed the transgenes at all stages of development. None of the transgenic plants produced by the method of this invention exhibited the transgene silencing phenomenon.

Our surprising results clearly demonstrate that the use of minimal transgene expression cassettes in combination with direct DNA transfer techniques, particularly particle bombardment, improves the frequency of generating transformed plants having transgenes in low copy number, a simple integration pattern with no more than a few integration sites, a reduced incidence of transgene silencing and stable expression of the transgene in plants all through development. To date we have not detected transgene silencing in any of the transgenic plants or in any of their progeny that have been analyzed.

The method disclosed herein may be applied to any plant tissue cell that can be transformed by direct DNA transfer techniques, particularly particle bombardment. Such plant tissue cells include, e.g., single cells, callus tissue (Type I and Type II), leaf discs, immature or mature embryos, meristem cells, root cells, hypocotyl cells and cotyledon cells, protoplasts or cell suspensions. Preferably, the protocols transform intact plant tissues, e.g., immature or mature embryo plant cells, callus cells (Type I and Type II), meristem cells, leaf cells, root cells, hypocotyl cells, cotyledon cells and shoot cells.

Also contemplated within the scope of this invention are food and animal feed products comprising the plants and their progeny and plant parts thereof. In addition, plants with agronomic, industrial, value added traits or alternative use traits are also contemplated.

Other aspects of the invention will be clear to the skilled artisan, and need not be set forth here. The terms and expressions which have been employed are used as terms of description and not of limitation, and one of skill in the art will recognize that various modifications are possible within the scope of the invention.

EXAMPLES

Example 1

Gene Constructs

Minimal expression cassettes were isolated after digestion of pWRG 2426 (Cooley et al. (1995)) with various combinations of the restriction enzymes XhoI and XbaI (bar), SalI and KpnI (hpt) and NotI (gusA) under conditions recommended by the supplier. Restriction digestions for each of the three chimeric genes were performed independently. Digestion of plasmid pWRG 2426 (9260 bp) with XhoI and XbaI yields three fragments: a 1896 bp fragment containing the chimeric bar gene, a 6950 bp fragment containing hpt, gusA and the vector sequences and a 414 bp sequence containing largely the CaMV35S promoter, which was driving the hpt gene. Digestion of pWRG 2426 with SalI and KpnI yields five fragments: a 2032 bp fragment containing the chimeric hpt gene, a 5787 bp fragment containing the gusA gene, the vector and the CaMV35S sequence driving the bar gene, and three small fragments of 253 bp, 313 bp and 875 bp. These three fragments contain parts of the chimeric bar gene. Digestion of pWRG 2426 with NotI yields two fragments: a 2628 bp fragment containing the chimeric gusA gene and the rest of the plasmid in a 6632 bp fragment. On either side of each gene cassette a few bp of vector a sequences are present. The bar gene cassette contains 32 bp before the start of the promoter and 3 bp after the end of the terminator. The hpt cassette contains 24 bp before the start of the promoter and 13 bp after the end of the terminator. The gusA cassette contains 19 bp before the start of the promoter and 16 bp after the end of the terminator.

Plant Material and Transformation

The procedures for preparing immature rice embryos (Oryza Sativa L.), the minimal transgene expression cassettes containing the bar, hpt or gusA sequences for bombardment, and the subsequent transformation and regeneration of transformed plants are described elsewhere (Christou et al., *Bio/Technology*, 9:957–962 (1991) incorporated in its entirety herein by reference).

Briefly, immature rice embryos 12–15 days old were harvested from expanded panicles and sterilized with 2% sodium hypochlorite for 5 minutes. They were subsequently rinsed repeatedly with sterile distilled water and the glumes were removed under aseptic conditions under a dissecting microscope and placed on MS medium (Murashige et al., *Plant Physiol.*, 15:473–497(1962)) or CC (Potrykus et al., *Theor. Appl. Genet.*, 54:209–214 (1979)) supplemented with 2,4-D at 0.5 or 2.0 mg/L with the adaxial side in contact with the medium (Datta et al., *Bio/Technology*, 8:736–740 (1990) supra; Hartke et al., *J. Genet. Breed.* 43:205–214 (1989)).

Mature seed-derived callus was prepared as described by Sudhakar et al. *Transgenic Res.*, 7:289–294 (1998) (incorporated in its entirety by reference). Rice seeds (Oryza sativa .ssp. indica) of diverse origin, CR-5272, M 7,ITA 212,IR 64,KDML 105, Basmati 370, M202, Jodon, Drew, Bengal, Cypress, Gulfmont, were dehusked and surface-sterilized in 70% ethanol for 3 minutes, then in a 50% sodium hypochlorite solution for 30 minutes, and rinsed in sterile distilled water. Seeds were placed in a petri dish containing 40 ml of culture medium for callus induction: MS basal medium supplemented with 2.5 mg/L 2,4-D, 3% (w/v) sucrose. The pH was adjusted to 5.8 before autoclaving at 120° C. for 20 minutes. Seeds were incubated in the dark at 27° C. Expanding mature embryos were separated from the endosperm 5–7 days after incubation. The explants were subjected to an osmotic treatment (mannitol 0.4 M) for 4 hours before and 16 hours after bombardment. Immediately prior to bombardment, tissue was secured on a prepared solid support.

Gold particles were coated with the linear minimal transgene expression cassettes as described for supercoiled plasmids according to the method of Christou et al. (1991) supra. For co-transformation experiments, we used a molar ratio of 1:3 hpt (selectable) to gusA (nonselected) cassettes. Particle bombardment and recovery of transgenic plants on selective medium supplemented with phosphinothricin (PPT) or hygromycin (hyg), was carried out as described previously (Klein et al., 1987; Sudhakar et al., 1998; Vain et al., 1998 incorporated in their entirety herein by reference). After bombardment, the explants were plated on fresh medium (supplemented with hygomycin 50 mg/L). Embryogenic calli plantlets were obtained every 15 days from the subculture of the calli resistant to 50 mg/L hygromycin. Selection pressure was maintained throughout the proliferation and regeneration phases of in vitro culture.

DNA Isolation

Leaf DNA was isolated using the cetyltrimethylammonium bromide (CTAB) DNA extraction method (Rogers et al., *Plant Molecular Biology Manual*, $2^{nd}$ Ed. 1:1–8 (1994), incorporated herein by reference). Briefly, leaf material was frozen in liquid nitrogen and was then ground in the presence of sea sand and 10 ml hot (60° C.) CTAB buffer (2% CTAB, 0.1MTris-HCl, pH 8.0, 0.02M $Na_2$-EDTA, 1.4M NaCl, 1% PVP). The slurry was incubated at 60° C. for one hour. Phenol/chloroform/isoamyl alcohol (25:24:1) mix was then added (10 ml). After thorough mixing, the slurry was centrifuged at 3000 rpm for 10 minutes to pellet the solid material. The supernatant was collected and one volume of iso-propanol added. After one hour at 4° C. the mix was centrifuged at 3000 rpm for 10 minutes to pellet the solids. The pellet was washed in 70% ethanol and after drying it was dissolved in 1 ml TE (Tris-Cl 10 mM:EDTA 1 mM).

Southern Blot Hybridization

Aliquots of genomic DNA (5 μg) were digested overnight with the appropriate restriction enzymes, (i.e., HindIII, EcoR1, Nhe1, Cla1, Sfi1, BstX1, Sal1 or Nco1) the digested DNA was fractionated by 0.8% agarose gel electrophoresis and alkali-blotted on to Hybond $N^+$ membranes (Amersham) according to the manufacturer's instructions. The linear transgene cassettes containing only the coding regions of tie bar, hpt or gusA genes isolated from pWRG 2426 were used as probes. Briefly, bar or hpt probe DNA (25 μg) was radiolabeled with $\alpha$-$^{32}$P-labeled dCTP (3000 Ci/mmol) by random primer method (Feinburg & Iogelstein, *Anal. Bioc.*, 137:266–267 (1994)). Southern blot hybridization was carried out as described previously (Kohli et al., *Proc. Natl. Acad. Sci. USA*, 95:7203–7208, (1998)). The filters were pre-hybridized and hybridized at 65° C. in the presence of high salt buffer, pH6.8 (3M NaCl/0.1M Pipes/0.02M $Na_2$EDTA), Denhardts solution and salmon sperm DNA (100 mg/ml of hybridization mix). The filters were subsequently washed twice in 2×SSC, 0.5% SDS and once in 0.2×SSC and 0.5% SDS, at 65° C. for 20 minutes and exposed to X-ray film. Autoradiography was carried out in a phosphoimager cassette for two days with Kodak XoMat X-ray film. The results are depicted in FIGS. 1–3.

Small Scale DNA Isolation for PCR

DNA was isolated from single leaflets, approximately 2 cm in length, according to the method of Edwards et al. "A simple and rapid method for the preparation of the plant genomic DNA for PCR analysis", *Nucleic Acids Research*, 19(6):1349 (1991).

Briefly, a single leaflet, approximately 2 cm long, was frozen in liquid nitrogen and ground in the presence of sea sand and 200 μl of extraction buffer (500 mM NaCl, 100 mM Tris-Cl (pH 8), and 50 mM $Na_2$EDTA (pH 8)) in a 1.5 ml microfuge tube to obtain a homogenate. Twenty microliter of 20% SDS was then added to the homogenate and mixed thoroughly. Another 200 μl of extraction buffer were added to homogenate.

A phenol/chloroform/isoamyl alcohol mix (25:24:1) was then added (400 μl) to the homogenate and mixed thoroughly again. The homogenate was then centrifuged in a microfuge at 13000 rpm for 5 minutes. The supernatant was collected and placed in a fresh tube. The volume of the supernatant was determined and an equal volume of isopropanol was added to the supernatant followed by a 1/10 volume of sodium acetate (pH 4.8). The DNA was pelletted by centrifugation at 13000 rpm and dried. The dried pellet was dissolved in 50 ml TE (10 mM Tris-Cl: 1 mM EDTA) and DNA concentration was estimated by running the samples on a 0.8% agarose gel. Approximately 50 to 70 ηg of DNA was used for PCR.

Since all three transgene cassettes (gusA, hpt and bar) were driven by CaMV35S promoter, each DNA sequence was amplified using the same forward primer, CaM F1: 5'-TAC AGT CTC AGA AGA CCA AA-3'(SEQ ID NO: 8), which anneals to the CaMV promoter. The bar and hpt cassettes contained the nos terminator, therefore these genes were amplified with reverse primer, Nos R1: 5'-AAT CAT CGC AAG ACC GGC AA-3'(SEQ ID NO: 9), which anneals to the nos terminator. The gusA cassette was amplified using a primer, Gus R1: 5'-GGG AGG CTA CAG ATG CTT TGC-3'(SEQ ID NO: 10), which anneals to the 3' end of the gusA coding sequence. We used a 25 µl total reaction volume comprising 50 mM KCl, 10 mM Tris-Cl (pH 8.2), 1 mM $MgCl_2$, 0.1 mM each of the four dNTPs, 100 nM each primer, 50–70 ng of genomic DNA and 1 unit of Taq DNA polymerase. The sequences were amplified under the following reaction conditions: denaturation at 95° C. for 5 min, then 30 cycles (94° C., 1 min; 60° C., 1 min; 72° C., 2 min) followed by 7 min final extension at 72° C.

The amplified PCR products were separated on 0.8% agarose gel containing EtBr. Separated PCR products were visualized under UV light and photographed. The molecular weight marker DNA used was the 1 Kb ladder from Pharmacia.

Enzyme Assays

Histochemical GUS assays were carried out as described by Jefferson et al. *EMBO J.* 6:3901–3907 (1987) incorporated herein by reference. Hygromycin phosphotransferase (HPT) assays were conducted by thin layer chromatography (TLC) according to the method of Datta et al. *Bio/technology*, 8:736–740 (1992), incorporated herein by reference.

Leaves (100–150 mg) were frozen in liquid nitrogen and ground using a mortar and pestle. Extraction buffer (0.5M Tris-Cl, pH 7.5, 10% glycerol, 0.1M phenyl methyl sulphonyl fluoride) was added (100 ml/100–150 mg of tissue) to the ground material. The samples were then centrifuged at 13000 rpm for 5 minutes at 4° C. to pellet the solids. The supernatant was collected (the crude extract) and stored −20° C. To assay for hygromycin phosphotransferase activity, 10 ml reaction mixture of 50 mM Tris-maleate pH 7.0, 50 mM $CaCl_2$, 0.05 mM ATP, 0.4 ml (g-32P) ATP (10 mCi/ml; 3000 Ci/mmol), 62 mg hygromycin-B and 5.6 ml of crude extract was incubated for 30 minutes at 37° C. One ml of the reaction was then applied to a PEI-cellulose thin layer chromatography (TLC) plate (Whatman). TLC was performed in 50 mM sodium formate/formic acid pH 5.4 as the liquid phase. The plates were allowed to dry and subjected to autoradiography.

Phosphinothricin acetyltransferase (PAT) TLC assays were performed as described by De Block et al., *EMBO J.*, 6:2513–2518(1987), incorporated herein by reference. One hundred mg of leaf tissue, 50–100 µl of extraction buffer (50 mM Tris-Cl, pH 7.5, 2 mM $Na_2EDTA$, 0.15 mg/ml leupeptine, 0.15 mg/ml of phenyl methyl sulphonyl fluoride (PMSF), 0.3 mg/ml bovine serum albumin (BSA) 0.3 mg/ml DTT) and 5 mg sea sand were mixed and ground in an Eppendorf tube to form a homogenate. The homogenate was centrifuged at 13000 rpm for 2 minutes. The supernatant was collected and centrifuged again at 13000 rpm for 5 minutes to eliminate any particulate matter and form a clarified extract. 12.5 µl of clarified extract were mixed with PPT (0.75 ml of a 1 mM stock in 50 mM Tris-Cl pH 7.5, 2 mM Na2EDTA) and AcCoA (1.25 µl, 14° C.) (58.1 mCi/mmol). The reaction mixture was incubated at 37° C. for 30 minutes. A six µl aliquot of the reaction mixture was then spotted on a silica-gel TLC plate. Ascending chromatography was carried out in a 3:2 mixture of 1-propanol and ammonium hydroxide (25% ammonia) at 14° C. and was visualized by autoradiography (XAR-5-Kodak film overnight).

Recovery of Transgenic Plants

A total of 108 independent transgenic rice plant lines transformed with the bar cassette, 42 lines transformed with the hpt cassette and 28 lines co-transformed with the hpt and gusA cassettes were obtained. PCR analysis was performed on all of the transgenic plants to confirm the presence of the bar or hpt cassettes as appropriate. The presence of the gusA cassette was verified by PCR and histochemical GUS assay.

Molecular Analysis of Bar Cassette Integration Patterns

A representative sample of 26 transgenic plants carrying the bar cassette was analyzed in detail. Genomic DNA from each of the transgenic lines was digested with HindIII, which cuts once at the 5' end of the bar cassette. Five enzymes that do not have recognition sites (non-cutters) within the cassette were also used (BstXI, ClaI, EcoRI, NheI and SfiI). These experiments allowed the determination of the number of transgenic loci in each line, provided an estimate of transgene copy number, and revealed the specific integration patterns for each primary transformant. The results are summarized in Table I.

Analysis of Southern blots hybridized with the bar probe revealed a single band in about 40% (9 out of 26) of the transformed plant lines when digested with HindIII and about 73% of the HindIII digested samples displayed very simple hybridization patterns (between one and three bands). There were only three plant lines that generated more than five hybridizing bands (A5-14, A5-15 and A13-2), when digested with HindIII (Table I).

In three of the plant lines (A19-12, A19-14 and A19-17) the single band observed when genomic DNA was digested with HindIII resolved into two bands when the DNA was digested with NheI, an enzyme that does not have a recognition site in the cassette (Table 1). This indicated that the single HindIII band did not necessarily represent a single transgene copy. As shown in Table 1, we obtained a single hybridizing band with at least one of the five non-cutter enzymes used, except in lines A 13-2 and A19-7. This indicated that in cases of multicopy integration events, all the integrating copies resided at a single transgenic locus.

FIG. 1 shows a Southern blot of genomic DNA from eight representative lines digested with SfiI or HindIII, and probed the bar coding sequence. The number of bands obtained after HindIII digestion ranged from 1–7, but in all cases SfiI digestion (which does not cut within the cassette) produced a single band, demonstrating cassette integration at a single site.

Molecular Analysis of hpt Cassette Integration Patterns

Analysis of transgenic plants carrying the hpt cassette revealed even simpler integration patterns. FIG. 2 shows a Southern blot of genomic DNA from 15 representative lines of the 42 generated. The DNA was digested with SalI, which has a single site at the 3' end of the cassette proximal to the 3' end of the nos terminator. Eight lines showed a single band, four showed two bands, and two lines showed multiple (more than five) bands. Six lines carrying the hpt cassette were analyzed in more detail using the non-cutters BstXI, ClaI, EcoRI, NheI, and SfiI. We obtained a single band in each of the six lines with at least one of the non-cutters.

Molecular Analysis of gusA Cassette Integration Patterns

Finally, we analyzed gusA cassette integration patterns resulting from co-transformation with separate hpt and gusA minimal linear cassettes. FIG. 3 shows a Southern blot of genomic DNA from 18 representative lines digested with NcoI, which cuts at a single site near the 5' end of the gusA coding region, and hybridized to gusA probe. We found that about 50% of the lines produced a single band, and none of the lines produced more than four bands. Thirteen of the eighteen lines displayed simple integration patterns. The observation of such simple integration patterns for both selected and nonselected transgene cassettes indicates that the patterns result from the nature of the exogenous DNA fragment and not from selection pressure arising during plant regeneration, which might favor high-expressers with simple transgene structures.

Analysis of Transgene Expression

PAT and HPT thin layer chromatography assays were performed to verify expression of the bar and hpt genes at different stages of development. Leaf samples were harvested at three stages of development: a) when the plant was transferred from rooting medium to soil; b) 40–45 days after the transfer to soil (before flowering) and c) 70–90 days after transfer to soil (after flowering). We detected PAT and HPT activities at all three stages. We used the histochemical GUS assay (Jefferson et al., 1987, supra, incorporated herein by reference) to detect GUS activity in callus lines, and observed GUS activity in all but two lines (Nip-1 and Nip-14) transformed with the gusA gene cassette. Expressed was monitored through to the R4 generation of transgenic plants and transgene expression remained stable in all lines.

TABLE 1

Summary of Southern blot results for transgenic lines containing the bar expression cassette

| Line No. | No. of Southern bands after cutting with restriction enzyme | | | | | |
|---|---|---|---|---|---|---|
| | HindIII | EcoRI | NheI | ClaI | SfiI | BstXI |
| A5-6 | 3 | 2 | 3 | 1 | nd | nd |
| A5-10 | 5 | 8 | 2 | 6 | nd | 1 |
| A5-11 | 5 | 7 | 1 | 4 | nd | nd |
| A5-14 | 9 | 7 | 2 | 3 | 1 | 5 |
| A5-15 | 7 | 4 | 3 | nd | 1 | 4 |
| A5-16 | 1 | 1 | 1 | 1 | 1 | 1 |
| A5-17 | 1 | 1 | 1 | 1 | 1 | 1 |
| A5-19 | 3 | 3 | 3 | 2 | 1 | nd |
| A5-22 | 3 | 7 | 2 | 2 | nd | 1 |
| A5-23 | 5 | 2 | 2 | 2 | 1 | 2 |
| A13-2 | 8 | 6 | 1 | 1 | 1 | 1 |
| A13-5 | 3 | 2 | 3 | 7 | nd | 2 |
| A13-7 | 2 | 2 | 2 | 2 | 1 | 1 |
| A19-5 | 1 | 1 | 1 | 1 | 1 | 1 |
| A19-7 | 4 | 11 | 2 | 3 | nd | — |
| A19-8 | 2 | 2 | 2 | 2 | 1 | 1 |
| A19-12 | 1 | 1 | 2 | 1 | 1 | 1 |
| A19-13 | 3 | 2 | 1 | 1 | nd | nd |
| A19-14 | 1 | 1 | 2 | 1 | 1 | 1 |
| A19-16 | 2 | 2 | 1 | 2 | 1 | 1 |
| A19-17 | 1 | 1 | 2 | 1 | 1 | 1 |
| A19-19 | 1 | 2 | 5 | 1 | 1 | 1 |
| A19-20 | 1 | 1 | 1 | 1 | 1 | 1 |
| A19-21 | 2 | 1 | 1 | 1 | 1 | 1 |
| A19-23 | 1 | 1 | 1 | 1 | 1 | 1 |
| A21-4 | 2 | 2 | 2 | 1 | 1 | 1 | nd, not determined

Example 2
Co-integration and Co-expression of Multiple Transgenes

Transgene Integration

Five different transgenes in the form of minimal transgene cassettes were co-transformed into rice tissue via particle bombardment as described supra. The transgene cassettes comprised a genetic marker, i.e., phosphinothricin acetyl transferase (bar), β-glucuronidase (gusA), hygromycin phosphotransferase (hpt), firefly luciferase (luc), or anthranilate synthase (as), a promoter and a terminator. The particular components of the various minimal transgene cassettes used in these experiments are displayed in Table 2.

Transgenic plants were selected for hygromycin resistance and were analyzed using PCR and Southern blots to determine the number of independent transformation events, the frequency of co-integration of 2 or more of the five transgenes, and the integration frequency of each of the transgenes. The expression of the various transgenes was also assayed.

Tables 3a, 3b and 3c summarize the integration and co-integration frequencies of the various transgenes. PCR and Southern blot analyses were used to analyze the integration of the transgenes within the plant genome.

TABLE 2

The minimal transgene cassettes used for transformation

| Gene | Promoter | Terminator |
|---|---|---|
| bar | CaMV 35s-Adh1 intron | Nopaline synthase (nos) |
| gusA | CaMV 35s | Rubisco Small subunit (ssu) |
| hpt | CaMV 35s | nos |
| luc | Ubi 1-ubi 1 intron | nos |
| as | Double CaMV 35s | CaMV |

Thirty eight independent transgenic plants, which integrated two or more different types of transgene cassettes, were recovered following co-transformation with the five minimal transgene cassettes by particle bombardment and selection for hygromycin resistance.

Table 3a displays the total number and percent of the transgenic plants that contained 2, 3, 4, or 5 transgenes integrated into their genome.

Table 3b displays the integration frequency of each transgene.

Table 3c displays the various combination of integrated transgenes and the frequency with which each combination was found in the thirty-eight plants. A variety of different transgene combinations were detected.

TABLE 3a

Cotransformation frequency of 2 or more transgenes

| Number of genes integrated | No. of plants out of 38 independent lines | Co-transformation frequency % |
|---|---|---|
| 2 | 6 | 16% |
| 3 | 15 | 39% |
| 4 | 11 | 29% |
| 5 | 6 | 16% |

TABLE 3b

Integration frequency for each transgene

| Integrated transgene | No. of plants out of 38 independent lines | Integration frequency % |
| --- | --- | --- |
| bar | 34 | 90% |
| gusA | 20 | 53% |
| hpt | 38 | 100% |
| luc | 15 | 40% |
| as | 24 | 63% |

TABLE 3c

Integration frequency of different transgene combinations

| Gene combination | No. of plants out of 38 independent lines | Frequency % |
| --- | --- | --- |
| hpt-bar | 3 | 8% |
| hpt-luc | 1 | 3% |
| hpt-as | 2 | 5% |
| hpt-bar-gus | 4 | 10% |
| hpt-bar-luc | 3 | 8% |
| hpt-bar-as | 7 | 18% |
| hpt-luc-as | 1 | 3% |
| hpt-bar-gus-luc | 4 | 10% |
| hpt-bar-gus-as | 6 | 16% |
| hpt-bar-luc-as | 1 | 3% |
| hpt-bar-gus-luc-as | 6 | 16% |

Transgene Expression

Expression of all five transgenes was determined at the mRNA level using RT-PCR or Northern blots. All transgene products, except for Anthranilate synthase, were assayed on the protein level by assaying for enzyme activity using standard techniques. Once expression of each of the transgenes in the various plants was determined, the results were tabulated to determine the frequency of co-expression of the transgenes in each plant. Twenty-four of the thirty eight transgenic plants (63%) co-expressed at least two integrated transgenes.

Table 4a displays the frequency of transgenic plants co-expressing two or more integrated transgenes, regardless of the identity of the transgene.

Table 4b displays the expression frequency for each of the integrated transgenes.

Table 4c depicts the number of the thirty-eight independent plant lines expressing various combinations of the five transgenes.

TABLE 4a

Co-expression of multiple transgenes

| Number of co-expressing genes | No. of plants out of 38 independent lines | Co-expression frequency % |
| --- | --- | --- |
| 2 | 9 | 24% |
| 3 | 10 | 26% |
| 4 | 4 | 11% |
| 5 | 1 | 3% |

TABLE 4b

Frequency of independent lines expressing specific transgenes

| Gene expressed | No. of independent lines expressing gene/No. of independent lines with gene integrated | Expression frequency % |
| --- | --- | --- |
| bar | 24/34 | 71 |
| Gus A | 10/20 | 50 |
| hpt | 38/38 | 100 |
| luc | 10/15 | 67 |
| as | 14/24 | 58 |

TABLE 4c

Frequency of co-expression of different transgene combinations

| Gene combinations | No. of plants out of 38 independent lines (Co-expression Frequency %) |
| --- | --- |
| hpt-bar | 8 (21%) |
| hpt-luc | 2 (5%) |
| hpt-as | 3 (8%) |
| hpt-bar-gus | 2 (5%) |
| hpt-bar-luc | 2 (5%) |
| hpt-bar-as | 6 (16%) |
| hpt-gus-luc | 1 (3%) |
| hpt-bar-gus-luc | 2 (5%) |
| hpt-bar-gusA-as | 2 (5%) |
| hpt-bar-gusA-luc-as | 1 (5%) |
| hpt-gus-luc-as | 2 (5%) |
| hpt | 7 (19%) |

We claim:

1. A method for producing a population of transgenic plants producing a desired product wherein less than about 20% of said transgenic plants undergo transgene silencing, said method comprising transforming intact plant cells with one, or more, minimal transgene expression cassette encoding the desired product by direct DNA transfer techniques and regenerating a population of transgenic plants from said transformed plant cells, and wherein less than about 20% of said transgenic plants undergo transgene silencing, wherein said minimal transgene expression cassette is a nucleic acid molecule encoding the desired product wherein no more than about 50 nucleotide pairs of the sequences in the nucleic acid molecule are sequences that do not encode or regulate expression of the desired gene product.

2. The method of claim 1, wherein the direct DNA transfer technique is selected from the group consisting of particle bombardment, microinjection, silicon carbide fiber transformation, the vortexing method and liposome mediated DNA uptake.

3. The method of claim 1, wherein the direct DNA transfer technique is particle bombardment.

4. The method of claim 1, wherein the minimal transgene expression cassette comprises no more than about 20 nucleotide pairs that are vector sequences.

5. The method of claim 1, wherein the minimal transgene expression cassette does not comprise vector sequences.

6. The method of claim 1, wherein the minimal transgene expression cassette comprises a genetic marker.

7. The method of claim 1, wherein the plant cell is co-transformed with a first minimal transgene expression cassette comprising a genetic marker and a second minimal transgene expression cassette comprising a transgene which is not the genetic marker in the first transgene expression cassette.

8. The method of claim 7, wherein the genetic marker encodes a product that confers resistance to an antibiotic, an herbicide, methotrexate, glyphosate or a metabolic inhibitor.

9. The method of claim 7, wherein the genetic marker encodes an enzyme selected from the group consisting of hygromycin phosphotransferase, phosphophinothricin acetyltransferase, neomycin phosphotransferase, kanamycin phosphotransferase, epsp synthase, acetolactate synthase, and mannose isomerase.

10. The method of claim 7, wherein the transgene of the first minimal transgene expression cassette is a genetic marker selected from the group consisting of hpt, bar, neo, luc, gus and Gfp.

11. The method of claim 1 wherein the transgene of the minimal transgene expression cassette encodes a seed storage protein.

12. The method of claim 1, wherein the transgene of the minimal transgene expression cassette encodes an antibody.

13. The method of claim 1, wherein the transgene of the minimal transgene expression cassette encodes an antibody fragment.

14. The method of claim 12, wherein the antibody fragment is selected from the group consisting of Fab', F(ab')$_2$, single chain Fv fragments, bispecific single chain Fv fragments and diabodies.

15. The method of claim 1, wherein the transgene of the expression cassette encodes an antisense RNA.

16. The method of claim 1, wherein the plant cells are from a monocotyledonous or a dicotyledonous plant.

17. The method of claim 1, wherein the plant cells are regenerable tissue.

18. The method of claim 17, wherein the plant cells are selected from the group consisting of embryo plant cells, callus cells, meristem cells, leaf cells, root cells, hypocotyl cells, cotyledon cells and shoot cells.

19. The method of claim 18, wherein the embryo plant cells are mature embryo seed cells or immature embryo cells.

20. The method of claim 18, wherein the callus cells are Type I or Type II callus cells.

21. The method of claim 16, where in the monocotyledonous plant is selected from the group consisting of barley, corn, millet, rice, sorghum, oat and wheat.

22. A method for producing a population of transgenic plants comprising a transgene expressing a desired product wherein said population of transgenic plants has a reduced percentage of transgenic plants that undergo transgene silencing as compared to a population of transgenic plants transformed by direct DNA transfer techniques using a whole or linearized vector comprising the transgene, said method comprising transforming intact plant cells with one, or more, minimal transgene expression cassette encoding the desired product by a direct DNA transfer technique and regenerating a population of transgenic plants from said transformed plant cells, wherein said minimal transgene expression cassette is a nucleic acid molecule comprising the transgene wherein no more than about 50 nucleotide pairs of sequence of the nucleic acid molecule do not encode or regulate expression of the desired gene product and wherein the population of transgenic plants transformed with the minimal transgene expression cassette has a reduced percentage of transgenic plants that undergo transgene silencing as compared to the population of transgenic plants transformed by direct DNA transfer techniques using the whole or linearized vector comprising the transgene.

23. The method of claim 22, wherein the direct DNA transfer technique is selected from the group consisting of particle bombardment, microinjection, silicon carbide fiber transformation, the vortexing method and liposome mediated DNA uptake.

24. The method of claim 22, wherein the direct DNA transfer technique is particle bombardment.

25. The method of claim 22, wherein the minimal transgene expression cassette comprises no more than about 20 nucleotide pairs that are vector sequences.

26. The method of claim 22, wherein the minimal transgene expression cassette does not comprise vector sequences.

27. The method of claim 22, wherein the minimal transgene expression cassette comprises a genetic marker.

28. The method of claim 22, wherein the plant cell is co-transformed with a first minimal transgene expression cassette comprising a genetic marker and a second minimal transgene expression cassette comprising a transgene which is not the genetic marker in the first transgene expression cassette.

29. The method of claim 28, wherein the genetic marker encodes a product that confers resistance to an antibiotic, an herbicide, methotrexate, glyphosate or a metabolic inhibitor.

30. The method of claim 28, wherein the genetic marker encodes an enzyme selected from the group consisting of hygromycin phosphotransferase, phosphophinothricin acetyltransferase, neomycin phosphotransferase, kanamycin phosphotransferase, epsp synthase, acetolactate synthase, and mannose isomerase.

31. The method of claim 28, wherein the transgene of the first minimal transgene expression cassette is a genetic marker selected from the group consisting of hpt, bar, neo, luc, gus and Gfp.

32. The method of claim 22, wherein the transgene of the minimal transgene expression cassette encodes a seed storage protein.

33. The method of claim 22, wherein the transgene of the minimal transgene expression cassette encodes an antibody.

34. The method of claim 22, wherein the transgene of the minimal transgene expression cassette encodes an antibody fragment.

35. The method of claim 34, wherein the antibody fragment is selected from the group consisting of Fab', F(ab')$_2$, single chain Fv fragments, bispecific single chain Fv fragments and diabodies.

36. The method of claim 22, wherein the transgene of the expression cassette encodes an antisense RNA.

37. The method of claim 22, wherein the plant cells are from a monocotyledonous or a dicotyledonous plant.

38. The method of claim 22, wherein the plant cells are regenerable tissue.

39. The method of claim 38, wherein the plant cells are selected from the group consisting of embryo plant cells, callus cells, meristem cells, leaf cells, root cells, hypocotyl cells, cotyledon cells and shoot cells.

40. The method of claim 39, wherein the embryo plant cells are mature embryo seed cells or immature embryo cells.

41. The method of claim 39, wherein the callus cells are Type I or Type II callus cells.

42. The method of claim 37, wherein the monocotyledonous plant is selected from the group consisting of barley, corn, millet, rice, sorghum, oat and wheat.

43. The method of claim 22 wherein the reduced percentage of transgenic plants that undergo transgene silencing is less than about 20%.

* * * * *